US00PP09142P

United States Patent [19]

Amador

[11] Patent Number: Plant 9,142

[45] Date of Patent: May 23, 1995

[54] ALSTROEMERIA PLANT NAMED DANIELA

[76] Inventor: Julio Amador, Calle 93, No. 19-25, Santafe De Bogota, Colombia

[21] Appl. No.: 195,768

[22] Filed: Feb. 10, 1994

[51] Int. Cl.[6] ..... A01H 5/00

[52] U.S. Cl. ..... Plt./87.1

[58] Field of Search ..... Plt. 87.1

*Primary Examiner*—James R. Feyrer

*Attorney, Agent, or Firm*—Christie, Parker & Hale

[57] ABSTRACT

A new and distinct alstroemeria variety producing numerous strong flowering stems and dark green leaves.

2 Drawing Sheets

BACKGROUND OF THE INVENTION

The present invention relates to a new and distinct cultivar of Alstroemeria originated as a seedling of unknown parentage discovered among my collection of alstroemeria varieties maintained under controlled conditions in a greenhouse in Sabana de Bogota—Madrid (Cund), Colombia for developmental purposes. The varietal denomination of the new variety is 'Daniela'.

The first act of asexual reproduction of 'Daniela' was by propagation of vegetative cuttings in Sabana de Bogota, Colombia. Asexual reproduction through successive generations has demonstrated that the combination of characteristics as herein disclosed for 'Daniela' are firmly fixed and retained through successive generations of asexual reproduction.

'Daniela' has not been observed under all possible environmental conditions. Phenotypic expression may vary significantly with variations in environment such as temperature, light intensity, day length and growing and cultural conditions.

SUMMARY OF THE INVENTION

Flowers of the new variety of Alstroemeria, 'Daniela', are of the butterfly type and are characterized by a partial lilac coloration against a white and greenish-white background along its petals. The petals also display purple spots and streaks of mainly dark but some of which are of light to dark coloration and of varying length. The plant produces numerous flowering stems, which is a desirable characteristic in a cut-flower variety. The flower-bearing stems are long, strong and of excellent quality. It has been established that 'Daniela' grows productively under polyplastic and under greenhouse conditions. The variety is reproducible by division of rhizomes and by tissue culture.

DESCRIPTION OF ILLUSTRATIONS

The new variety of Alstroemeria is illustrated in the accompanying illustrations, which show typical flower and foliage characteristics, with colors being as nearly true as is possible for illustrations of this type.

The first sheet of drawing contains a first photograph which shows a single blossom of the plant in close view to illustrate the relative sizes and shapes of the outer and inner sets of petals (tepals), as well as the differences in coloration and spotting patterns of each set.

The second and the third photographs each depict the stand of the claimed plant in commercial monoculture. The top photograph is a perspective showing the lush, vigorous growth of a crop of Daniela in a greenhouse bed. The bottom photograph shows new and old foliage of the plant and the breaking action of new branches in the same greenhouse bed where the plants have been heavily cropped. Both of these photographs show the nearly constant formation of new flowering stems under greenhouse conditions.

DETAILED DESCRIPTION OF THE NEW VARIETY

The following is a detailed description of the new cultivar of Alstroemeria as observed during the month of August in a greenhouse in Bogota, Colombia at an elevation of over 2,500 meters above sea level. Color designations indicated are in accordance with The Royal Horticultural Society Colour Chart by color plate designations.

Botanical classification:

*Family.*—Amaryllidaceae.

*Genus.*—*Alstroemeria sp.*

Origin: Seedling.

PLANT

Form: Parabolic upright, branched at the top.

Growth: Vigorous.

Branching: Floral stems proceed from subterraneous rhizomes.

Flower stem:

*Length.*—Nominal length about 127 cm.

*Color.*—Near 137D.

Foliage:

*Quantity.*—About 17 — abundant.

*Size of leaf.*—Length — about 12 cm. Width — about 2.9 cm.

*Shape of leaf.*—Lanceolate.

*Texture.*—Leaf top side — bright, silky. Leaf underside — easily corrugated.

*Color.*—Leaf top side — near 137A. Leaf underside — near 137C.

*Venation.*—Parallel veins — 7 main, 8 secondary, disposed longitudinally, prominent on the surface.

*Stem color.*—Near 137D.

*Rhizomes.*—Color — Near 155A. Size — about 2 cm minimum length.

BUD

Form (shape): Rhomboid to ellipsoid.

Size: About 2.5 cm in diameter.

Calyx (shape): Hexagonal with prominent nervures, 3 sepals, elliptic, cucullate and greenish when unripe.

Opening rate: Average to 100% opening.

FLOWER

Blooming habit: Continuous.

Flower:

*Size.*—About 6.0 cm.

*Diameter.*—About 5.2 cm.

*Depth.*—About 5.5 cm.

*Borne.*—2 days for bud onset.

Inflorescence:

*Shape.*—Umbrella, umbel-like, 4-8 rays, some of them secondarily branched.

*Color.*—Near 70B.

Peduncle:

*Length.*—About 5 to 6 cm.

*Color.*—Near 73A.

Bloom:

*Type.*—Butterfly.

*Petalage.*—6 petals, an outer set of three emarginate or heart-shaped, petals; an inner set of three oblanceolate petals imbricated over the three outer petals; because there are 6 tepals, they are described in group: 3 outer tepals (sepals), alternated with three inner tepals (the true petals), all the tepals (both sepals and petals) are attached to the floral receptacle or torus.

*Arrangement of petals.*—The outer set comprises 2 lateral and 1 upper emarginate petals of comparable shape and appearance, the inner set comprises 2 upper oblanceolate petals about as long, but only about half the width of the outer petals, and 1 bottom oblanceolate petal of approximately half the length and width of the 2 upper, inner petals

*Size* (fully expanded).—Outer tepals, to 5 cm long and 2.4 cm wide; inner tepals-the two adaxial tepals enlarged and imbricated (to 5 cm long); the adaxial one smaller (to 4.4 cm long).

*Shape.*—Heart-shaped outer petals, widely obovate, the apex emarginate; all of them are cupped shaped.

*Texture of petals.*—Soft, but the base of the tepals, and the base and the apex of the outer ones are thick.

*Aspect.*—Smooth, minutely crimped at margin.

*Lasting quality.*

After cutting.—About 11 days.

Color:

*Flower coloration.*—Each petal of the outer set has near white ground color, and the red-purple brush stroke of near 63C extending from the point of attachment to the middle of the petal and a green brush stroke extending from the tip of the apex that fades to near white at the middle of the petal; the brush strokes are essentially confined to the central portion of the petal lamina, with the lateral marginal portions being essentially white; the apical lobes are tinted pink most intensively at the margin and suffusing gradually to the near white of the remainder of the marginal portions; the outer petals contain elongated markings of near 59A, which are essentially confined to the white marginal portions; inner petals are substantially of white ground color and have suffusions of light pink at the top and bottom portions of the petals, with a light greenish-yellow band suffused into central portions of the petals; elongated markings of near 59A are randomly expressed about surfaces of the inner petals.

Underside of petal coloration: Each petal has near white ground color 155B with a wide brush stroke of near 55C and a green edge near 144A. Stripes of near 59A are primarily confined to the wide marginal portion. A light pinkish tinge near 56B is present on the lower petal edge closest to the apex.

*Discoloration as bloom ages.*—Stable (firm), strong.

REPRODUCTIVE ORGANS

Stamens:

*Number.*—6, near 197A.

Anthers:

*Size.*—About 0.6 cm by 0.3 cm.

*Color.*—Near 197A.

Filaments:

*Length.*—About 38 mm stamens.

*Color.*—Near 78C.

Pollen:

*Color.*—Near 102B.

Pistils:

*Number.*—1.

*Styles.*—Length — about 6 cm. Color — near 73B.

*Stigmas.*—Color — near 73B.

Character of ovaries: Ovary inferior, with 3 carpolo and 3 locules; placentation axile; ovules numerous.

Calyx:

*Shape.*—Polycarpal.

*Size.*—About 1 cm in length and about 0.8 cm in diameter.

I claim:

1. A new variety of Alstroemeria plant substantially as herein shown and described.

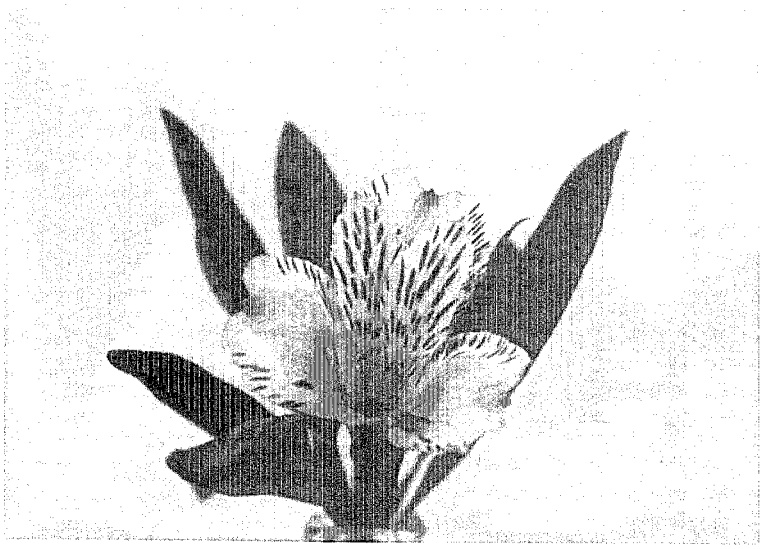

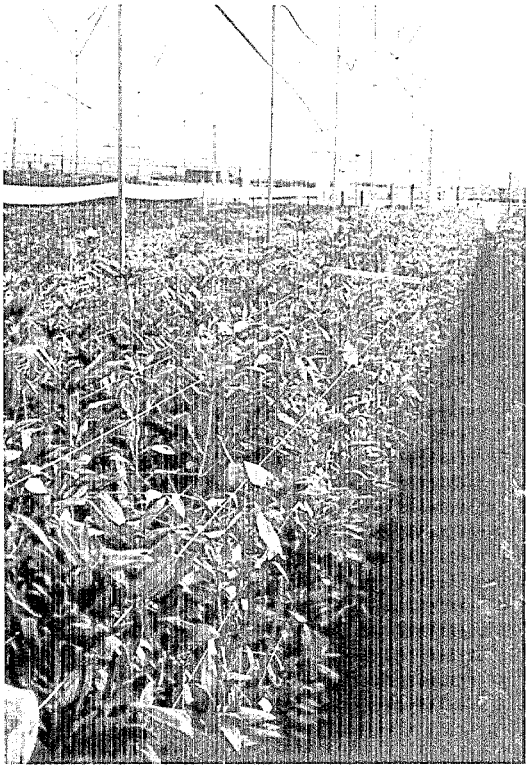
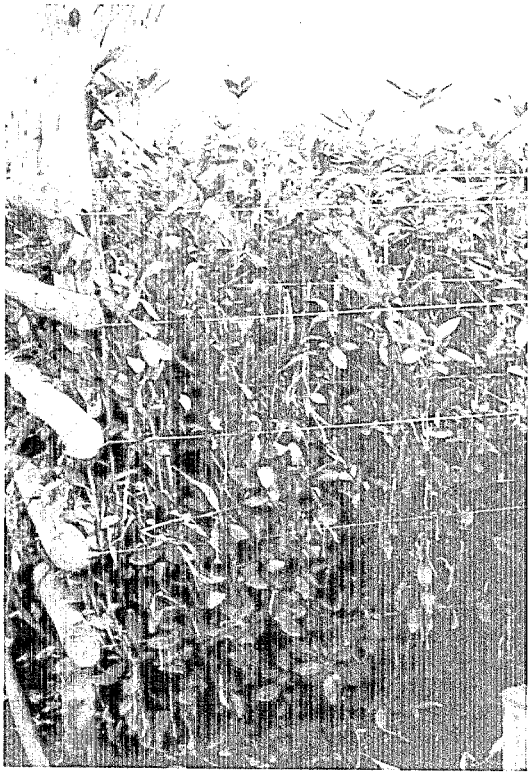

* * * * *